United States Patent [19]

Grey et al.

[11] Patent Number: 5,081,268
[45] Date of Patent: Jan. 14, 1992

[54] PROCESS FOR THE PREPARATION OF OXETANES FROM 1,3-GLYCOL MONOSULFATES

[75] Inventors: Roger A. Grey; Lawrence J. Karas; H. Dean Moore, Jr., all of West Chester, Pa.

[73] Assignee: Arco Chemical Technology, Inc., Wilmington, Del.

[21] Appl. No.: 563,023

[22] Filed: Aug. 6, 1990

[51] Int. Cl.$^5$ .......................................... C07D 305/06
[52] U.S. Cl. ................................... 549/510; 549/511
[58] Field of Search ............................... 549/510, 511

[56] References Cited

U.S. PATENT DOCUMENTS 3,006,926 10/1961 Case et al. ........................... 549/510

OTHER PUBLICATIONS

J. Am. Chem. Soc. 79 (1957) 948, p. 1, fourth paragraph (Searles et al.).
Bull. Soc. Chim. Fr. (1972) 4655, p. 2, second paragraph (Halary et al.).
J. Organometal. Chem. 47 (1973) 337, p. 2, third paragraph (Delmond et al.).
Bull. Soc. Chim. Fr. (1971) 3501, p. 2, third paragraph (Combret et al.).
Tetrahedron Letters (1973) 4459, p. 2, third paragraph (Castro et al.).
Nature, Aug. 13, 1960, s 592, p. 3, second paragraph (Case).

Primary Examiner—C. Warren Ivy
Assistant Examiner—Ba K. Trinh
Attorney, Agent, or Firm—Jonathan L. Schuchardt

[57] ABSTRACT

A practical, selective process for preparing oxetanes is disclosed. A 1,3-glycol monosulfate salt is prepared by sulfation and neutralization of the corresponding 1,3-glycol. The neutral monosulfate salt is then reacted with a strong base, resulting in efficient ring closure to the oxetane.

50 Claims, No Drawings

PROCESS FOR THE PREPARATION OF OXETANES FROM 1,3-GLYCOL MONOSULFATES

FIELD OF INVENTION

This invention relates to a process for preparing oxetanes. According to the invention, a 1,3-glycol is converted to a neutral 1,3-glycol monosulfate salt. The monosulfate salt is then reacted with a strong base to form the oxetane. The method is simple, economical, and gives high selectivity to oxetanes.

BACKGROUND OF THE INVENTION

Oxetanes are a class of organic compounds that contain a four-membered ring containing one oxygen atom. The small ring size and high degree of ring strain associated with oxetanes makes them readily polymerizable, yet difficult to synthesize. Thus, although 1,4-butanediol can be readily cyclodehydrated to give tetrahydrofuran under mild acid conditions, 1,3-propanediol when reacted under similar conditions gives no oxetane. Although polymers from oxetanes may have interesting properties, their commercialization has had only limited success because of the unavailability of highly selective, practical, economical methods for synthesizing oxetanes.

Many syntheses of oxetanes have been developed, but side reactions are common, and yields are typically less than 50 percent. In addition, the products are difficult to purify.

Searles et al. (*J. Am. Chem. Soc.*, 79 (1957) 948) reported a synthesis of oxetanes by conversion of a 1,3-glycol to the corresponding gamma-chlorohydrin acetate, followed by ring closure with boiling aqueous caustic. The glycol is reacted with acetyl chloride and thionyl chloride prior to ring closure. Although this is one of the more commonly used methods of synthesizing oxetanes, yields are usually poor (20–40%), and substantial proportions of elimination products can be formed if the starting glycol has a hydrogen attached at the 2-carbon.

Reaction of 1,3-glycols with phosgene or dialkyl carbonates gives cyclic carbonates of the glycols, which can be cracked with bases or transition metal catalysts to give carbon dioxide and the desired oxetane. Halary et al. (*Bull. Soc. Chim. Fr.* (1972) 4655) showed that cyclic carbonates decompose in the presence of catalysts such as lithium chloride and silver cyanide to give oxetanes in about 30 percent yield. More recently, Bartok et al. (*Acta. Chim. Hung.* 114 (1983) 375) demonstrated that oxetanes could be produced by pyrolysis at 320° C. of the carbonate in the presence of potassium cyanide. These methods typically give substantial amounts of side products in addition to the desired oxetane, and are therefore of limited value.

In addition, oxetanes have been synthesized from many esoteric intermediates, such as gamma-haloalkoxytributylstannanes (B. Delmond et al., *J. Organomet. Chem.* 47 (1973) 337), gamma-halogenated magnesium alkoxides (J. Combret et al., *Bull. Soc. Chim. Fr.* (1971) 3501), and gamma-hydroxyalkoxyphosphonium salts (B. Castro et al., *Tetrahedron Lett.* (1973) 4459. While these reactions are interesting and unusual, they are of limited practical value.

A commercially more interesting route to oxetanes is taught by Case (U.S. Pat. No. 3,006,926, and *Nature*, Aug. 13, 1960, p. 592). A sulfuric acid solution of a 1,3-glycol is added to boiling caustic, and the oxetane product is distilled from the reaction mixture. The yields of oxetanes are relatively low—only about 30 percent at best. In addition, numerous side reactions can occur depending upon the structure of the glycol. For example, if 2-methyl-1,3-propanediol is used in practicing this method, a substantial amount of methallyl alcohol is generated as a by-product.

Clearly, alternative methods for synthesizing oxetanes are needed. Methods involving simple, inexpensive reagents are required so that the synthesis can be carried out on a commercial scale. Methods that give the desired oxetane products in high yield and in the absence of rearrangement or elimination products are especially needed.

SUMMARY OF THE INVENTION

The present invention provides a method for preparing an oxetane from a neutral 1,3-glycol monosulfate salt. The monosulfate salt is cyclized to form an oxetane salt by treatment with a strong base. The reaction is general; any of the three carbons of the 1,3-glycol monosulfate can have linear, branched, or cyclic alkyl, aryl or aralkyl substituents.

The 1,3-glycol monosulfate salt is prepared by reacting a 1,3-glycol with a sulfating agent, followed by neutralization with an amine or alkali metal compound. The sulfating agent can be acidic, such as sulfuric acid or sulfur trioxide/dichloromethane, or essentially neutral, such as a sulfur trioxide/amine adduct.

The strong base used to cyclize the salt typically has a pH in aqueous solution of greater than about 12, and is typically an alkali metal hydride, hydroxide, alkoxide, or the like.

When an essentially neutral 1,3-glycol monosulfate salt is cyclized, the reaction is highly selective, and by-products generated in other ring-closure procedures are avoided.

DETAILED DESCRIPTION OF THE INVENTION 1,3-Glycols have been used traditionally as the ultimate starting materials for oxetanes. Precursor compounds are usually prepared because of the difficulty of cyclizing the 1,3-glycols directly. The precursor compounds of this invention are 1,3-glycol monosulfate salts prepared by reacting the corresponding 1,3-glycols with sulfating agents.

Both the sulfation reaction and ring-closure step are general for a wide variety of substituted and unsubstituted 1,3-glycol starting materials. The 1,3-glycols have the general structure:

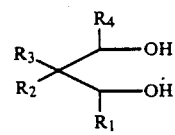

wherein $R_1$, $R_2$, $R_3$ and $R_4$ may be the same or different and are selected from the group consisting of hydrogen, $C_1$–$C_{24}$ linear, branched, and cyclic alkyl, aralkyl, and aryl. Examples of suitable groups for $R_1$–$R_4$ include, but are not limited to, hydrogen, methyl, ethyl, propyl, isopropyl, butyl, tert-butyl, isobutyl, n-pentyl, cyclopentyl, cyclohexyl, benzyl, phenyl, methylphenyl, chlorophenyl, naphthyl, and the like.

Particularly preferred 1,3-glycols for use in the process of the invention include 1,3-propanediol, 2-methyl-1,3-propanediol, 2,2-dimethylpropanediol, pentane-2,4-diol, 2-ethyl-1,3-propanediol, 2,2-diethyl-1,3-propanediol, 2-phenyl-1,3-propanediol, 2,2-bis(-chloromethyl)-1,3-propanediol, 2,2-diphenyl-1,3-propanediol, and 2,4-dimethylpentane-2,4-diol.

Sulfating agents useful in the practice of the invention are compounds capable of exchanging an $SO_3$-containing moiety for an alcohol hydrogen. Examples of suitable sulfating agents include, but are not limited to sulfur trioxide/ether adducts, sulfur trioxide/amine adducts, sulfur trioxide/amide adducts, sulfur trioxide/phosphate adducts, sulfur trioxide, sulfur trioxide/sulfur dioxide mixtures, chlorosulfonic acid, sulfuric acid, fuming sulfuric acid, sulfuric acid/acetic anhydride, and sulfamic acid, and the like, and mixtures thereof. Many of the sulfating agents are highly acidic, either in the Bronsted or Lewis sense, and give rise to acidic products having at least one sulfonic acid end group. Sulfur trioxide and sulfuric acid are typical examples. Other sulfating agents, including some of the sulfur trioxide-/Lewis base adducts, are fairly neutral, and give rise to fairly neutral 1,3-glycol monosulfate-Lewis base adducts. Examples include sulfur trioxide/pyridine and sulfur trioxide/dimethylformamide.

When a sulfur trioxide/Lewis base adduct is used, the molar ratio of 1,3-glycol to sulfating agent is preferably within the range of about 0.6:1.0 to 2.0:1.0. More preferably, the range is about 0.75:1.0 to 1.25:1.0.

The sulfation step is typically carried out in an organic solvent, but depending upon the sulfating agent, can be run without a solvent. Reaction of the 1,3-glycol with the sulfating agent is usually performed at temperatures within the range of about $-80°$ C. to $75°$ C. Solubility limitations, cooling costs, and reduced reaction rates make sulfation temperatures below about $-80°$ C. rather impractical. Above about $75°$ C., undesirable side reactions such as rearrangement or elimination can occur; these side reactions tend to adversely affect selectivity to the desired oxetane products in the ring-closure step. A preferred temperature range for the sulfation reaction is from about $-20°$ C. to $40°$ C. An especially preferred range is from about $10°$ C. to $30°$ C.

The sulfation step is typically carried out in a substantially moisture-free, inert atmosphere of argon, nitrogen, or the like. The order of addition of the sulfating agent and 1,3-glycol is not critical. Usually, the sulfating agent is a liquid and is added in small proportions over a period of time to the 1,3-glycol to facilitate removal of heat from the reaction mixture. The reaction mixture is maintained at the desired reaction temperature by any suitable means. External cooling or heating means may be used as needed to regulate the reaction temperature.

The reaction mixture following sulfation of a 1,3-glycol will typically contain the desired 1,3-glycol monosulfate, a proportion of unreacted 1,3-glycol, and some 1,3-glycol disulfate. This result is difficult to avoid because the hydroxyl groups often have approximately the same reactivity toward the sulfating agent. The desired monosulfate is typically neutralized and then isolated if desired from the other reaction products by any suitable means, including fractional crystallization or selective precipitation from one or more solvents. A particularly preferred method of purifying the monosulfate salt is described in Example 4 below. The mixture of products is dissolved in hot methanol and filtered to remove inorganic sulfate salts. Most of the disulfate precipitates from methanol upon cooling. The monosulfate is then isolated from unreacted 1,3-glycol by a series of precipitations from isopropanol wherein the 1,3-glycol remains primarily in the mother liquor. Essentially 100% pure monosulfate can be isolated. The purified, neutral monosulfate salt may then be used in the cyclization step discussed below. Alternatively, the reaction mixture containing glycol, monosulfate, and disulfate can be neutralized and then used without further purification in the cyclization step. The cyclization is usually not adversely affected by the presence of the disulfate or glycol components.

Following sulfation, an effective amount of an amine or alkali metal compound is added to generate a neutral 1,3-glycol monosulfate salt having the formula:

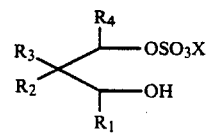

In accordance with the invention, X is selected from the group consisting of sodium, lithium, potassium, ammonium, pyridinium, and organoammonium. Examples of amines suitable for use as neutralizing agents include, but are not limited to, ammonia, ammonium hydroxide, pyridine, methylamine, dimethylamine, diethylamine, trimethylamine, triethylamine, tributylamine, cyclohexylamine, and the like, and mixtures thereof. The alkali metal compounds used as neutralizing agents are typically alkali metal hydroxides or alkoxides. Examples include sodium hydroxide, lithium hydroxide, potassium hydroxide, sodium methoxide, potassium methoxide, and the like, and mixtures thereof.

In the cyclization step, a neutral 1,3-glycol monosulfate salt is reacted with a strong base to produce an oxetane. The strong base has a pH in aqueous solution of greater than about 12. Normally, the strong base is selected from the group consisting of alkali metals, alkali metal hydrides, alkali metal hydroxides, alkali metal alkyls, alkali metal alkoxides, alkali metal amides, and organoammonium hydroxides. For reasons of cost, availability, and effectiveness, alkali metal hydroxides are preferred. Sodium hydroxide and potassium hydroxide are particularly preferred. Examples of strong bases suitable for use in the process of the invention include, but are not limited to, sodium metal, potassium metal, sodium hydroxide, lithium hydroxide, sodium hydride, potassium hydride, methyl lithium, n-butyl lithium, sodium methoxide, potassium methoxide, sodium ethoxide, sodium amide, potassium amide, tributylammonium hydroxide, and the like, and mixtures thereof.

Ordinarily, an excess molar amount of the strong base is used in the cyclization compared with the amount of neutral 1,3-glycol monosulfate salt. Preferably, the monosulfate salt and strong base are employed in an equivalent ratio of from about 1.0:1.0 to 1.0:5.0. More preferably, the monosulfate salt:strong base ratio is from about 1.0:1.2 to 1.0:2.0. The relative amount of strong base employed will depend upon a number of factors, including reaction temperature and identity of the cationic moiety (X) of the neutral 1,3-glycol monosulfate salt.

If desired, a crown ether such as 18-crown-6 or 12-crown-5 can be added to the reaction mixture to accelerate the rate of the cyclization reaction or to improve selectivity to the oxetane product.

The reaction of the neutral 1,3-glycol monosulfate salt with the strong base is performed at a temperature sufficient to effect ring closure to the oxetane with elimination of an inorganic sulfate salt. The reaction temperature required will depend upon a number of factors, including, among other things, the structure of the monosulfate salt, the nature of the strong base, and the concentration of reactants. Typically, the reaction is carried out at a temperature within the range of about 50° C. to 200° C. At temperatures below 50° C., the reaction rate is usually too slow to be of practical value. Undesirable side reactions such as rearrangement or elimination tend to become quite important contributors to the reaction products at temperatures greater than about 200° C. A preferred temperature range for performing the ring closure is from about 85° C. to 130° C. Particularly preferred is a range from about 95° C. to 120° C.

Cyclization of the neutral 1,3-glycol monosulfate salt can be performed in the presence of water or an organic solvent. Ordinarily, the choice is made on the basis of the solubility of the reactants. 1,3-Glycol monosulfates having relatively few nonpolar substituents will cyclize well in aqueous solution, while monosulfates with numerous nonpolar substituents will tend to cyclize better in organic solvents such as tetrahydrofuran. Particularly preferred organic solvents for the cyclization include alcohols, glycols, and glycol monoethers. Examples of such preferred solvents include 1-phenylethanol, 2-butoxyethanol, dipropylene glycol monomethyl ether, 1-tert-butoxy-2-propanol, 4-tert-butoxy-1-butanol, 3-tert-butoxy-2-methyl-1-propanol, dipropylene glycol, and the like, and mixtures thereof.

Since the oxetane products are normally much more volatile than either the corresponding 1,3-glycols or monosulfate salts, the oxetanes are preferably and conveniently separated from the reaction mixture by distillation as they are generated. Continuous removal is preferred over batch removal for two reasons: (1) the oxetane is removed before it can undergo ring-opening polymerization or elimination reactions, and (2) continuous removal helps to drive the ring-closure reaction to completion. The distillation is typically performed at atmospheric or reduced pressure depending upon the volatility of the oxetane. Nonvolatile oxetanes can be purified by other suitable means that are well known in the art, such as selective extraction with solvents, recrystallization, or chromatography.

Removal of the oxetane by distillation may be facilitated by the use of a high-boiling, inert, suspending liquid. The suspending liquid will have a boiling point significantly higher than the oxetane product, so that when the mixture is distilled, the oxetane separates cleanly from the higher-boiling components. Preferably, the inert suspending liquid has a normal boiling point—a boiling point at atmospheric pressure—of greater than about 90° C. The suspending liquid helps to keep the reaction mixture stirrable, and permits more complete isolation of the oxetane from the reaction mixture. The optimum suspending liquid depends on many factors, but most importantly the desired polarity and the boiling point of the oxetane. Any high-boiling liquid that is inert under the strongly basic cyclization reaction conditions may be used. Examples of suitable suspending fluids include high-boiling saturated hydrocarbons, mineral oil, polyalkylene glycol ethers such as tetraglyme and tripropylene glycol dimethyl ether, halogenated and nonhalogenated aromatic compounds such as dichlorobenzene and mesitylene, and the like, and mixtures thereof. Once isolated from the cyclization reaction mixture, the oxetane product may optionally be dried with any commercially available drying agent, such as magnesium sulfate or potassium carbonate, and redistilled any desired number of times to enhance purity.

The following examples are presented to assist the skilled artisan in practicing the invention. It should be apparent that many variations on the examples within the spirit of the invention are possible. The examples are provided, therefore, for illustration and are not meant to limit the claims.

Examples 1–4 illustrate how various sulfating reagents can be used to prepare 1,3-glycol monosulfates from the corresponding 1,3-glycols. In each example, the product is neutralized with an alkali metal hydroxide to produce the neutral 1,3-glycol monosulfate salts useful as starting materials for the oxetanes. Example 4 shows how a mixture containing unreacted glycol and disulfate in addition to the desired monosulfate can be purified to give clean monosulfate. The fact that clean monosulfate is not necessary for the cyclization to be effective is shown in Example 33.

Cyclization of 2-methyl-1,3-propanediol sodium monosulfate to 3-methyloxetane was performed under a variety of conditions within the scope of the present invention. The results are illustrated in Examples 5–30 and in Tables 1 and 2. Table 1 shows preparations using aqueous media, while Table 2 summarizes the ring closure results with various alcohol, glycol, and alkoxyalcohol solvents. Gas chromatography yields of 3-methyloxetane as high as 68% were achieved. Importantly, selectivity to 3-methyloxetane was excellent—typically 93 to 99 percent. The predominant volatile side-products, methallyl alcohol and isobutyraldehyde, were typically 0 to 7 percent of the total volatiles. These could be almost completely eliminated by selecting the proper reaction conditions (compare Examples 7 and 12).

Comparative Example 23 shows how 3-methyloxetane can be prepared using a related prior art method. The isolated yield of 95% pure 3-methyloxetane was 10%. Substantial amounts of methallyl alcohol and isobutyraldehyde were generated, as evidenced by GC analysis of the distillation pot residue.

2,4-Dimethyloxetane and 3,3-dimethyloxetane were also prepared according to the process of the invention. These are shown in Examples 31 and 32.

EXAMPLE 1

Preparation of 2-Methyl-1,3-propanediol Sodium Monosulfate using Sulfur Trioxide/Dioxane A 3-neck 500-mL round bottom flask equipped with a thermometer, magnetic stir bar, addition funnel, and argon inlet was charged with dioxane (250 mL). Dichloromethane (9 mL) and liquid sulfur trioxide (10.0 g, 0.125 mol) were charged to the addition funnel. The sulfur trioxide solution was added to the dioxane at room temperature. The temperature of the reaction mixture was kept below 30° C.

A one-liter 3-neck round bottom flask equipped with a mechanical stirrer, thermometer, addition funnel, and argon inlet was charged with 2-methyl-1,3-propanediol (11.5 g, 0.128 mol). The sulfur trioxide/dioxane solution prepared above was added to this solution over 10 minutes while maintaining the reaction mixture at 25° C. The mixture was allowed to react at 25° C. for 30 minutes, and then an aliquot was removed. The aliquot was neutralized with 20% aqueous sodium hydroxide solution. Isopropanol was added, and the sample was rotary evaporated to dryness and dried in a vacuum oven (60° C., 1 torr) overnight. Carbon-13 nuclear magnetic resonance (NMR) spectroscopic analysis showed 18% of 2-methyl-1,3-propanediol, 18% of the corresponding disulfate, and 65% of the desired 2-methyl-1,3-propanediol sodium monosulfate salt.

EXAMPLE 2

Preparation of 2-Methyl-1,3-propanediol Sodium Monosulfate using Sulfur Trioxide/N,N-Dimethylformamide A 3-neck 500-mL round bottom flask equipped with a thermometer, magnetic stir bar, addition funnel, and argon inlet was charged with N,N-dimethylformamide (DMF) (125 mL). Dichloromethane (9 mL) and liquid sulfur trioxide (10.0 g, 0.128 mol) were charged to the addition funnel. The sulfur trioxide solution was added to the N,N-dimethylformamide solution dropwise while maintaining the reaction mixture below 30° C. by external cooling.

A 3-neck one-liter round bottom flask equipped with a mechanical stirrer, thermometer, addition funnel, and argon inlet was charged with 2-methyl-1,3-propanediol (11.5 g, 0.128 mol) and N,N-dimethylformamide (50 mL) and cooled to $-25°$ C. The sulfur trioxide/DMF solution prepared above was added to the glycol solution dropwise over 10 minutes while maintaining the temperature of the reaction mixture at $-25°$ C. After completion of the addition, the mixture was allowed to react for 30 more minutes. Aqueous sodium hydroxide (20%) solution was added at $-25°$ C. to neutralize the mixture. Isopropanol was added, and the solvents were removed by rotary evaporation. The solids were dried in a vacuum oven (60° C., 1 torr) overnight. Analysis by carbon-13 NMR showed 3% of 2-methyl-1,3-propanediol, 31% of disulfate, and 66% of the desired 2-methyl-1,3-propanediol sodium monosulfate.

EXAMPLE 3

Preparation of 2,2-Dimethyl-1,3-propanediol Sodium Monosulfate

A 500-mL, 3-neck round bottom flask equipped with a thermometer, argon inlet, magnetic stir bar, and stopper was charged with 2,2-dimethyl-1,3-propanediol (20.8 g, 200 mmol) and dichloromethane (200 mL). The clear solution was cooled to 10° C. using an ice-water bath. Sulfur trioxide/pyridine complex (32.0 g, 200 mmol) was added under argon in one portion via solid addition funnel. The mixture quickly warmed to 17° C. from the exothermic reaction. After 30 minutes of stirring, thin-layer chromatography analysis indicated that a small amount of diol remained. This was consumed by addition to the reaction mixture of more sulfur trioxide/pyridine complex (1.6 g, 10 mmol). After another 30 minutes of stirring, the clear, reddish-brown solution was transferred to a single-neck, one-liter round bottom flask. Solvents were removed under reduced pressure to afford 54.0 g of a thick, brownish oil. The pH of this product was 3.5.

The brown oil was filtered through a short pad of silica gel using 10% methanol/chloroform as the eluant. Solvents were removed under reduced pressure to afford a white solid. TLC analysis indicated that this material consisted of the desired monosulfate containing small amounts of disulfate as a contaminant. The mixture was dissolved in acetone and filtered to remove the insoluble disulfate. Removal of the acetone gave the desired pyridinium monosulfate salt.

The pyridinium monosulfate salt was dissolved in water (200 mL) and neutralized with 10% aqueous sodium hydroxide to a pH of 10.2. Removal of water under reduced pressure gave 2,2-dimethyl-1,3-propanediol sodium monosulfate as a white solid (15.2 g, 82% yield).

EXAMPLE 4

Preparation of Pure 2-Methyl-1,3-propanediol Sodium Monosulfate

A 3-liter, 3-neck round bottom flask equipped with a mechanical stirrer, thermometer, addition funnel, and argon inlet was charged with 2-methyl-1,3-propanediol (360 g, 4.0 mol). Sulfuric acid (96%) (400 g, 3.9 mol) was added to the diol at a rate to maintain the temperature of the reaction mixture at 35° C. The addition required about 30 minutes. The reaction mixture was stirred for an additional 24 hours. Carbon-13 NMR analysis of a sample revealed 30% diol, 52% monosulfate, and 18% disulfate. The reaction mixture was cooled to 5° C. and diluted with deionized water (500 mL) while maintaining the temperature below 25° C. The solution was cooled again to 5° C., and neutralized with 20% aqueous sodium hydroxide solution (200 g, 5.0 mol) to pH=10 while maintaining the temperature below about 25° C. About 1 liter of water was removed by vacuum distillation, whereupon solids precipitated to give an unstirrable mixture. Isopropanol (2 liters) was added to the solids to give a slurry. Isopropanol and water were removed together by rotary evaporation. The sequence of isopropanol addition followed by stripping was repeated twice more. The residue was treated with hot (50° C.) methanol (3 liters). The undissolved solids, believed to be mostly sodium sulfate, were separated by filtration. The filtrate was allowed to stand at room temperature to precipitate mostly 2-methyl-1,3-propandiol disulfate salt, which was then separated. The filtrate was stripped using a rotary evaporator until solids began to precipitate while the mixture was still hot. After cooling overnight, the white precipitate that formed was separated by filtration and stripped of methanol. Isopropanol (3 liters) was added to the residue, and the white precipitate was filtered and washed with isopropanol. These solids (batch I), which contained only 2-methyl-1,3-propanediol and the desired monosulfate salt, were saved. The filtrate was rotary evaporated to a thick slurry and isopropanol (1 liter) was added to the slurry to form white solids that were filtered and washed with isopropanol. These solids (batch II) were also saved. The filtrate was again reduced by rotary evaporation and treated with isopropanol to generate more white solids (batch III), which were filtered and washed as previously described. The three batches of solids were separately dried in a vacuum oven for 24 h (60° C., 1 torr). Carbon-13 NMR analysis showed 84% monosulfate and 16% 2-methyl-1,3-propanediol in each batch. The three batches of dried solids were combined and washed 3 times with isopropanol (300 mL) and dried in a vacuum oven for 24 hours. These solids were again washed with isopropanol and dried in the vacuum oven to constant weight to give 245 grams of a white solid. Carbon-13 NMR showed only the desired monosulfate. No diol or disulfate was found.

EXAMPLE 5

Preparation of 3-Methyloxetane from 2-Methyl-1,3-propanediol Sodium Monosulfate

A 3-neck 500-mL round bottom flask equipped with a mechanical stirrer, thermometer, and distillation head was charged with sodium hydroxide (56 g, 1.4 mol), deionized water (200 mL), and 2-methyl-1,3-propanediol sodium monosulfate (135 g, 0.70 mol). The reactor was placed in an oil bath at 120° C. The temperature of the reaction mixture rose to about 113° C., and volatile products were removed by distillation. After about 2 h, the overhead temperature reached about 100° C. and the reaction was stopped. Pentane (200 mL) was added to the distillate, and the aqueous phase was saturated with sodium chloride. The layers were separated. The pentane layer was dried over anhydrous magnesium sulfate, filtered, and distilled at atmospheric pressure to give 11 g of 99% pure 3-methyloxetane (22% yield).

EXAMPLES 6–19

Preparation of 3-Methyloxetane from 2-Methyl-1,3-propanediol Sodium Monosulfates using Aqueous Alkali Metal Hydroxides A glass pressure vessel was charged with 2-methyl-1,3-propanediol sodium monosulfate (3.8 g), deionized water (10 g), and an alkali metal hydroxide base as shown in Table 1. The percent yields reported are gas chromatography yields using dioxane as a standard added to an aliquot of the aqueous reaction mixture. Selectivities are based only on three products: 3-methyloxetane (MO), methallyl alcohol (MA), and isobutyraldehyde (i-BA). 18-Crown-6 (4.0 mole percent based on the amount of monosulfate salt) was included in Examples 16 and 17.

TABLE 1

| | | | 3-Methyloxetane Synthesis | | |
|---|---|---|---|---|---|
| Ex # | Temp (°C.) | Time (h) | Base (eq) | % Yield | MO/MA/i-BA |
| 6 | 120 | 18 | NaOH (1) | 27 | 94/5/1 |
| 7 | 120 | 16 | NaOH (2) | 40 | 99/0/0 |
| 8 | 120 | 6 | NaOH (2) | 58 | 96/4/0 |
| 9 | 120 | 2 | NaOH (2) | 28 | 94/5/1 |
| 10 | 120 | 4 | NaOH (2) | 59 | 96/3/1 |
| 11 | 120 | 4 | KOH (1) | 28 | 96/3/1 |
| 12 | 120 | 4 | KOH (2) | 48 | 99/0/1 |
| 13 | 120 | 4 | KOH (3) | 51 | 96/3/1 |
| 14 | 120 | 4 | KOH (4) | 54 | 97/2/1 |
| 15 | 120 | 4 | LiOH (2) | 13 | 97/1/2 |
| 16 | 120 | 4 | NaOH (2) 18-Cr-6 | 36 | 92/6/1 |
| 17 | 120 | 4 | KOH (2) 18-Cr-6 | 43 | 96/3/1 |
| 18 | 120 | 4 | NaOH (4) | 66 | 96/3/1 |
| 19 | 100 | 16 | NaOH (2) | 30 | 95/4/1 |

EXAMPLES 20–30

Preparation of 3-Methyloxetane from 2-Methyl-1,3-propanediol Sodium Monosulfate in Alcohol, Glycol, and Alkoxyalcohol Solvents A glass pressure tube was charged with 2-methyl-1,3-propanediol sodium monosulfate (1.9 g), sodium hydroxide (1.25 or 2.0 equivalents), and an alcohol or alkoxyalcohol solvent (7.0 g) as indicated in Table 2. The tubes were heated at 120° C. for 4 hours. The percent yields recorded in Table 2 were determined by gas chromatography (GC). An aliquot of the reaction mixture was combined with a known amount of dioxane and diluted with enough water to make a homogeneous solution prior to GC analysis. The selectivities reported in Table 2 are based only on three products: 3-methyloxetane (MO), methallyl alcohol (MA), and isobutyraldehyde (i-BA)

TABLE 2

| | 3-Methyloxetane Synthesis using Alcohol Solvents | | | |
|---|---|---|---|---|
| Ex. # | Solvent | NaOH (eq) | % Yield | MO/MA/i-BA |
| 20 | methanol | 1.25 | 18 | 95/4/1 |
| 21 | t-butanol | 1.25 | 22 | 85/8/7 |
| 22 | 1-phenylethanol | 1.25 | 65 | 93/5/2 |
| 23 | 2-(methoxyethoxy)ethanol | 1.25 | 30 | 94/3/3 |
| 24 | 2-butoxyethanol | 2.00 | 51 | 93/7/0 |
| 25 | dipropylene glycol monomethyl ether | 2.00 | 67 | 93/6/1 |
| 26 | 1-t-butoxy-2-propanol | 1.25 | 67 | 94/3/3 |
| 27 | 1-t-butoxy-2-propanol | 2.00 | 68 | 94/3/3 |
| 28 | 4-t-butoxy-1-butanol | 2.00 | 48 | 90/5/5 |
| 29 | 3-t-butoxy-2-methyl-1-propanol | 2.00 | 62 | 92/7/1 |
| 30 | dipropylene glycol | 2.00 | 43 | 93/7/0 |

EXAMPLE 31

Preparation of 2,4-Dimethyloxetane

A glass pressure tube was charged with 2,4-pentanediol sodium monosulfate (5.15 g, 25 mmol), sodium hydroxide (3.0 g, 75 mmol), and water (25 mL). The reaction mixture was heated at 150° C. for 4 h, then analyzed by gas chromatography. The GC yield of 2,4-dimethyloxetane was 10%.

EXAMPLE 32

Preparation of 3,3-Dimethyloxetane from 2,2-Dimethylpropane-1,3-diol Sodium Monosulfate A 3-neck, 500-mL round bottom flask equipped with a reflux condenser, magnetic stir bar and argon inlet was charged with potassium hydride (2.0 g, 80 mmol), tetrahydrofuran (75 mL) and 2,2-dimethylpropane-1,3-diol sodium monosulfate (9.4 g, 72 mmol). The reaction mixture was heated at reflux for 4 h. Removal of the solvent by distillation gave the alkoxide salt of the monosulfate. Tetradecane (50 mL) was added to the solids, and the slurry was heated at 120° C. The distillate was collected in a Dean-Stark trap to give 3,3-dimethyloxetane (1.0 g, 20% yield).

EXAMPLE 33

Preparation of 3-Methyloxetane from a Mixture of 2-Methyl-1,3-propanediol Sodium Monosulfate with Diol and Disulfate A glass pressure tube was charged with an aqueous solution (25 g) that analyzed for 3.25 g of 2-methyl-1,3-propanediol sodium monosulfate, 2.4 g of disulfate, and 1.35 g of 2-methyl-1,3-propanediol. Potassium hydroxide (3.0 g) was added, and the mixture was heated to 120° C. for 4 h. GC analysis indicated a 38% yield of 3-methyloxetane based on the amount of monosulfate salt initially present.

COMPARATIVE EXAMPLE 34

Preparation of 3-Methyloxetane—Sulfuric acid/Hot Caustic method

A 3-neck, one-liter flask equipped with a mechanical stirrer, thermometer, addition funnel, and argon inlet was charged with 2-methyl-1,3-propanediol (200 g, 2.22 mol). Sulfuric acid (96%) (233 g, 2.28 mol) was added to the diol over 1 h via addition funnel while maintaining the reaction temperature at about 35° C. This solution was used immediately in the next step.

A 4-neck, 3-liter flask equipped with a mechanical stirrer, thermometer, addition funnel, and distillation head was charged with sodium hydroxide (270 g, 6.75 mol) dissolved in deionized water (225 mL) (55% caustic). This solution was heated to 105° C. and the diol/sulfuric acid mixture described in the preceding paragraph was added dropwise. A vigorous reaction occurred with foaming, and the reaction temperature rose quickly to 130° C. The overhead temperature rose quickly to 75° C. as the oxetane product distilled. Addition of the diol/acid solution was complete in one hour, during which time the pot temperature dropped to 118° C. and the overhead temperature rose to 100° C. The reaction mixture was heated for an additional 2 h, during which time the pot temperature was increased gradually to 150° C., and the overhead temperature reached 110° C. The combined distillate fractions (350 g), which contained mostly water and 3-methyloxetane, were extracted with pentane (5×100 mL) and dichloromethane (2×100 mL). The combined extracts were dried over anhydrous calcium chloride and distilled at atmospheric pressure. GC analysis of the distillation pot after most of the solvent was removed showed 12% of isobutyraldehyde, 84% of 3-methyloxetane, and 4% of methallyl alcohol. The fractions boiling between 68° C. and 71° C. were collected to give 95% pure 3-methyloxetane (16 g, 10% yield).

We claim:

1. A process for producing an oxetane comprising: reacting a neutral 1,3-glycol monosulfate salt having the formula:

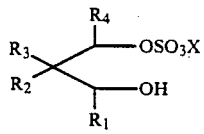

with an effective amount of a strong base to produce the oxetane; wherein X is selected from the group consisting of sodium, lithium, potassium, ammonium, pyridinium, and organoammonium; $R_1$, $R_2$, $R_3$, and $R_4$, which may be the same or different, are selected from the group consisting of hydrogen, $C_1$-$C_{24}$ linear, branched, and cyclic alkyl, aralkyl, and aryl; and the strong base has a pH in aqueous solution of greater than about 12.

2. The process of claim 1 wherein $R_1$, $R_2$, $R_3$, and $R_4$ are hydrogen.

3. The process of claim 1 wherein $R_1$, $R_2$, and $R_4$ are hydrogen, and $R_3$ is methyl.

4. The process of claim 1 wherein $R_1$ and $R_4$ are methyl, and $R_2$ and $R_3$ are hydrogen.

5. The process of claim 1 wherein $R_1$ and $R_4$ are hydrogen, and $R_2$ and $R_3$ are methyl.

6. The process of claim 1 wherein the strong base is selected from the group consisting of alkali metal hydrides, alkali metals, alkali metal hydroxides, alkali metal alkyls, alkali metal alkoxides, alkali metal amides, and organoammonium hydroxides.

7. The process of claim 1 wherein the strong base is selected from the group consisting of sodium hydroxide and potassium hydroxide.

8. The process of claim 1 wherein the 1,3-glycol monosulfate salt and strong base are employed in an equivalent ratio of from about 1.0:1.0 to 1.0:5.0.

9. The process of claim 1 wherein the process is conducted in the presence of water.

10. The process of claim 1 wherein the process is conducted in an organic solvent.

11. The process of claim 10 wherein the organic solvent is selected from the group consisting of alcohols, alkoxyalcohols, and glycols.

12. The process of claim 10 wherein the organic solvent is selected from the group consisting of 1-phenylethanol, dipropylene glycol monomethyl ether, 1-t-butoxy-2-propanol, 3-t-butoxy-2-methyl-1-propanol, and 2-butoxyethanol.

13. The process of claim 1 wherein the process is conducted in the presence of an inert suspending liquid having a boiling point at atmospheric pressure of greater than about 90° C.

14. The process of claim 1 wherein the reaction is performed at a temperature of from about 50° C. to 200° C.

15. The process of claim 1 wherein X is sodium and the strong base is an alkali metal hydroxide.

16. The process of claim 1 wherein the reaction is performed in the presence of a crown ether.

17. The process of claim 1 wherein the oxetane is continuously removed by distillation.

18. The process of claim 1 wherein the reaction mixture also contains a glycol and/or a disulfate having the formula:

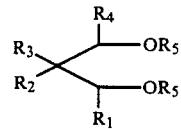

wherein $R_5$ is selected from the group consisting of hydrogen and —$SO_3X$.

19. A process for producing an oxetane comprising:
(a) reacting a 1,3-glycol having the formula:

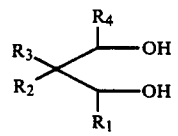

with a sulfating agent to form a 1,3-glycol monosulfate;

(b) neutralizing the 1,3-glycol monosulfate with an effective amount of an amine or alkali metal compound to produce a neutral 1,3-glycol monosulfate salt having the formula:

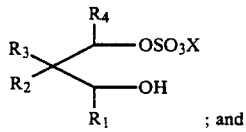

; and (c) reacting the neutral 1,3-glycol monosulfate salt with a strong base to produce the oxetane;

wherein X is selected from the group consisting of sodium, lithium, potassium, ammonium, pyridinium, and organoammonium; $R_1$, $R_2$, $R_3$, and $R_4$, which may be the same or different, are selected from the group consisting of hydrogen and $C_1$–$C_{24}$ linear, branched, or cyclic alkyl, aralkyl, and aryl; and the strong base has a pH in aqueous solution of greater than about 12.

20. The process of claim 19 wherein the sulfating agent is selected from the group consisting of sulfur trioxide/ether adducts, sulfur trioxide/amine adducts, sulfur trioxide/amide adducts, sulfur trioxide/phosphate adducts, sulfur trioxide, sulfur trioxide/sulfur dioxide mixtures, chlorosulfonic acid, sulfuric acid, fuming sulfuric acid, sulfuric acid/acetic anhydride, and sulfamic acid.

21. The process of claim 19 wherein the reaction of the 1,3-glycol with the sulfating agent is carried out at a temperature within the range of about −80° C. to 75° C.

22. The process of claim 19 wherein the molar ratio of the 1,3-glycol and the sulfating agent is from about 0.6:1.0 to 2.0:1.0.

23. The process of claim 19 wherein the sulfating agent is an acidic sulfating agent selected from the group consisting of sulfuric acid, chlorosulfonic acid, fuming sulfuric acid, sulfamic acid, sulfur trioxide/sulfur dioxide mixtures, and sulfur trioxide.

24. The process of claim 19 wherein step (c) is conducted in the presence of water.

25. The process of claim 19 wherein step (c) is conducted in the presence of an organic solvent.

26. The process of claim 25 wherein the organic solvent is selected from the group consisting of alcohols, alkoxyalcohols, and glycols.

27. The process of claim 26 wherein the organic solvent is selected from the group consisting of 1-phenylethanol, dipropylene glycol monomethyl ether, 1-t-butoxy-2-propanol, 3-t-butoxy-2-methyl-1-propanol, and 2-butoxyethanol.

28. The process of claim 19 wherein step (c) is conducted in the presence of an inert suspending liquid having a boiling point at atmospheric pressure of greater than about 90° C.

29. The process of claim 19 wherein step (c) is performed at a temperature within the range of about 50° C. to 200° C.

30. The process of claim 19 wherein the strong base is selected from the group consisting of sodium hydroxide and potassium hydroxide.

31. The process of claim 19 wherein $R_1$, $R_2$, $R_3$, and $R_4$ are hydrogen.

32. The process of claim 19 wherein $R_1$, $R_2$, and $R_4$ are hydrogen, and $R_3$ is methyl.

33. The process of claim 19 wherein $R_1$ and $R_4$ are methyl, and $R_2$ and $R_3$ are hydrogen.

34. The process of claim 19 wherein $R_1$ and $R_4$ are hydrogen, and $R_2$ and $R_3$ are methyl.

35. The process of claim 19 wherein the reaction mixture of step (c) also contains a glycol and/or a disulfate having the formula:

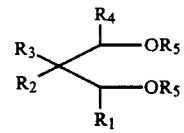

wherein $R_5$ is selected from the group consisting of hydrogen and —$SO_3X$.

36. A process for producing an oxetane comprising:
(a) reacting a 1,3-glycol having the formula:

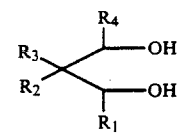

with an effective amount of a sulfur trioxide/Lewis base adduct to form a 1,3-glycol monosulfate-Lewis base adduct;

(b) reacting the 1,3-glycol monosulfate-Lewis base adduct with an effective amount of an amine or alkali metal compound to produce a neutral 1,3-glycol monosulfate salt having the formula:

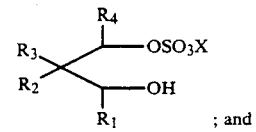

; and (c) reacting the neutral 1,3-glycol monosulfate salt with a strong base to produce the oxetane;

wherein X is selected from the group consisting of sodium, lithium, potassium, ammonium, pyridinium, and organoammonium; $R_1$, $R_2$, $R_3$, and $R_4$, which may be the same or different, are selected from the group consisting of hydrogen and $C_1$–$C_{24}$ linear, branched, or cyclic alkyl, aralkyl, and aryl; and the strong base has a pH in aqueous solution of greater than about 12.

37. The process of claim 36 wherein the sulfur trioxide/Lewis base adduct is selected from the group consisting of sulfur trioxide/amine adducts, sulfur trioxide/ether adducts, sulfur trioxide/amide adducts, and sulfur trioxide/phosphate adducts.

38. The process of claim 36 wherein the sulfur trioxide/Lewis base adduct is selected from the group consisting of sulfur trioxide/dioxane and sulfur trioxide/N,N-dimethylformamide.

39. The process of claim 36 wherein the reaction of the sulfur trioxide/Lewis base adduct with the 1,3-glycol is performed at a temperature from about −80° C. to 75° C.

40. The process of claim 33 wherein the molar ratio of the 1,3-glycol and the sulfur trioxide/Lewis base adduct is from about 0.6:1.0 to 2.0:1.0

41. The process of claim 36 wherein $R_1$, $R_2$, $R_3$ and $R_4$ are hydrogen.

42. The process of claim 36 wherein $R_1$, $R_2$, and $R_4$ are hydrogen and $R_3$ is methyl.

43. The process of claim 36 wherein $R_1$ and $R_4$ are hydrogen, and $R_2$ and $R_3$ are methyl.

44. The process of claim 36 wherein $R_1$ and $R_4$ are methyl, and $R_2$ and $R_3$ are hydrogen.

45. The process of claim 36 wherein the reaction mixture of step (c) also contains a glycol and/or a disulfate having the formula:

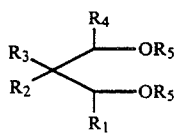

wherein $R_5$ is selected from the group consisting of hydrogen and $-SO_3X$.

46. The process of claim 36 wherein step (c) of the process is conducted in the presence of water.

47. The process of claim 36 wherein step (c) of the process is conducted in the presence of an organic solvent.

48. The process of claim 47 wherein the organic solvent is selected from the group consisting of alcohols, alkoxyalcohols, and glycols.

49. The process of claim 48 wherein the organic solvent is selected from the group consisting of 1-phenylethanol, dipropylene glycol monomethyl ether, 1-t-butoxy-2-propanol, 3-t-butoxy-2-methyl-1-propanol, and 2-butoxyethanol.

50. The process of claim 36 wherein step (c) of the process is conducted in the presence of an inert suspending liquid having a boiling point at atmospheric pressure of greater than about 90° C.

* * * * *